United States Patent
Kodama et al.

(10) Patent No.: US 8,563,468 B2
(45) Date of Patent: Oct. 22, 2013

(54) COLOR DEVELOPING COMPOSITION CONTAINING MOLECULAR COMPOUND, AND RECORDING MATERIAL

(75) Inventors: Satoshi Kodama, Ichihara (JP); Kazumi Jyujyo, Kisarazu (JP)

(73) Assignee: Nippon Soda Co., Ltd., Tokyo (JP)

( * ) Notice: Subject to any disclaimer, the term of this patent is extended or adjusted under 35 U.S.C. 154(b) by 296 days.

(21) Appl. No.: 13/055,855

(22) PCT Filed: Aug. 3, 2009

(86) PCT No.: PCT/JP2009/003694
§ 371 (c)(1),
(2), (4) Date: Jan. 25, 2011

(87) PCT Pub. No.: WO2010/016228
PCT Pub. Date: Feb. 11, 2010

(65) Prior Publication Data
US 2011/0120345 A1    May 26, 2011

(30) Foreign Application Priority Data
Aug. 4, 2008  (JP) .................................. 2008-201328

(51) Int. Cl.
B41M 5/333 (2006.01)
(52) U.S. Cl.
USPC ........................................ 503/216; 106/31.18
(58) Field of Classification Search
None
See application file for complete search history.

(56) References Cited

U.S. PATENT DOCUMENTS 5,801,288 A * 9/1998 Fujii et al. ....................... 568/33

FOREIGN PATENT DOCUMENTS

| EP | 0 764 635 | * | 3/1997 |
|----|-----------|---|--------|
| JP | A-08-333329 |   | 12/1996 |
| JP | 10-29969 | * | 2/1998 |
| JP | A-11-005776 |   | 1/1999 |
| JP | 2002-255925 | * | 9/2002 |
| JP | A-2003-305959 |   | 10/2003 |
| JP | B2-3936775 |   | 6/2007 |

OTHER PUBLICATIONS

International Preliminary Report on Patentability in International Application No. PCT/JP2009/003694; dated Mar. 8, 2011.
International Search Report in International Application No. PCT/JP2009/003694; dated Sep. 15, 2009 (with English-language translation).

* cited by examiner

Primary Examiner — Bruce H Hess
(74) Attorney, Agent, or Firm — Oliff & Berridge, PLC

(57) ABSTRACT

Provided is a color-developing composition containing a molecular compound which has as a component compound a compound represented by formula (I)

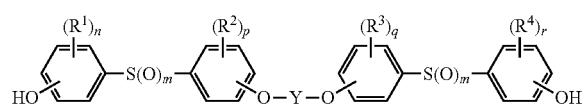

(I)

[wherein Y represents a C1-C12 hydrocarbon group which is chained or branched and saturated or unsaturated, or a C1-C8 hydrocarbon group which is chained or branched, saturated or unsaturated and has an ether or thioether bond; $R^1$, $R^2$, $R^3$ and $R^4$ each independently represent a C1-C6 alkyl group or C2-C6 alkenyl group; n, p, q and r each represents any integer of 0 to 4; and m represents any integer of 0 to 2]. Also provided is a recording material with a sufficient color-forming sensitivity, superior storage stability, and especially with an extremely little background fogging in a heat resistance test.

6 Claims, 4 Drawing Sheets

COLOR DEVELOPING COMPOSITION CONTAINING MOLECULAR COMPOUND, AND RECORDING MATERIAL

TECHNICAL FIELD

The present invention relates to color-developing compositions and recording materials that contain a molecular compound comprising a diphenylsulfone derivative and the like as a component compound. The present application claims priority to Japanese Patent Application No. 2008-201328 filed on Aug. 4, 2008, the content of which is hereby incorporated by reference.

BACKGROUND ART

Recording materials that utilize color formation resulted by reaction of a color-forming compound and a color-developing agent makes it possible to carryout recording in a short time with a relatively simple device without conducting cumbersome treatments such as developing/fixing. Such recording materials are thus widely used for thermal recording papers used for output recording such as for a facsimile and a printer, as well as for pressure sensitive copying papers used for simultaneous copying multiplicate sheets. As for these recording materials, those are desired wherein color is formed swiftly, whiteness of the no color-forming part (hereinafter referred to as "background") is preserved, and toughness of the color-formed image and the background is high. Further, recording materials have recently been used in large quantities in the areas such as labels where credibility of the recorded images weigh heavily, and those recording materials have been strongly desired that provide color-formed images with superior storage stability against a plasticizer, fats, etc. contained in the organic high-molecular materials used for packaging. Under such circumstances, it has been studied from various aspects to solve the problems associated with not only color-forming compounds and color-developing agents but also development of various adjuvants such as storage stabilizers and the like. However, sufficiently satisfactory solutions have not yet been found.

As a compound similar to that of the present invention, there is a recording material using such as a diphenylsulfone derivative represented by formula (I).

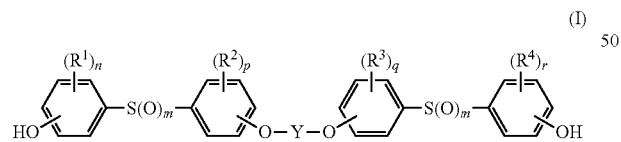

Such recording material, however, was not yet satisfactory in respect of the image storage stability, etc. (Patent Document 1).

On the other hand, a molecular compound for use in the present invention is described in Patent Document 2, while its use as a recording material is not described therein. Therefore, value of that molecular compound as a recording material has been left unknown.

[Patent Document 1] Japanese Laid-Open Patent Application No. 8-333329

[Patent Document 2] Japanese Patent No. 3936775

DISCLOSURE OF THE INVENTION

Object to be Solved by the Invention

As mentioned above, storage stability of the color-formed image has been expected for recording materials, and particularly expected recently is to improve plasticizer resistance and oil resistance. The object of the present invention is to provide a recording material which not only has a storage stability for the color-formed image but also has a sufficient color-forming density, superior property for keeping background whiteness, and, in particular, superior property for keeping background heat resistance.

Means to Solve the Object

The present inventors have made a keen study to solve the above-mentioned problems and found that by using, as a color-developing composition, a molecular compound comprising a compound represented by formula (I) as a component compound, a recording material can be obtained which has a sufficient color-forming sensitivity, superior storage stability, and, especially, extremely little background fogging in a background heat resistance test. The present invention is thus completed.

Specifically, the present invention relates to: (1) a color-developing composition containing a molecular compound, wherein the molecular compound comprises as a component compound a compound represented by formula (I)

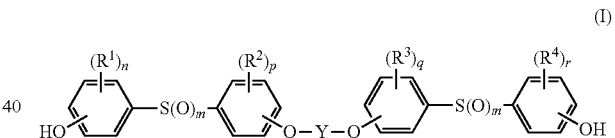

[wherein Y represents a C1-C12 hydrocarbon group which is chained or branched and saturated or unsaturated, or a C1-C8 hydrocarbon group which is chained or branched, saturated or unsaturated and has an ether or thioether bond, or represents the following formula

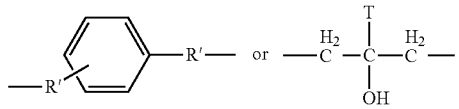

(wherein R's may be the same or different and each represents a methylene group or ethylene group; T represents a hydrogen atom or a C1-C4 hydrocarbon group); $R^1$, $R^2$, $R^3$ and $R^4$ each independently represent a C1-C6 alkyl group or C2-C6 alkenyl group; n, p, q and r each represents any integer of 0 to 4; and m represents any integer of 0 to 2].

The present invention further relates to (2) the color-developing composition according to (1), wherein the compound represented by formula (I) is a compound represented by formula (II)

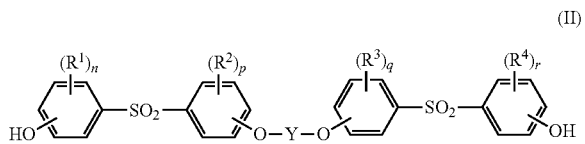

(II)

(wherein Y, $R^1$-$R^4$, n, p, q and r have the same meaning as defined above); and (3) the color-developing composition according to (1) or (2), wherein the compound represented by formula (I) is 2,2'-bis[4-(4-hydroxyphenylsulfonyl)phenyloxy]diethylether.

The present invention further relates to: (4) the color-developing composition according to any one of (1) to (3), wherein the color-developing composition is a composition containing 2 or more types of products obtained by reacting 4,4'-dihydroxydiphenylsulfone and 2,2'-dichlorodiethylether; and (5) the color-developing composition according to any one of claims 1 to 4, which contains a molecular compound consisting of 2,2'-bis[4-(4-hydroxyphenylsulfonyl)phenyloxy]diethylether and a compound capable of forming a molecular compound with the diethylether, wherein the molecular compound is obtained by mixing following (A) and (B):

(A) a product obtained by reacting 4,4'-dihydroxydiphenylsulfone and 2,2'-dichlorodiethylether;

(B) a compound capable of forming a molecular compound with 2,2'-bis[4-(4-hydroxyphenylsulfonyl)phenyloxy]diethylether.

The present invention still further relates to (6) a recording, material containing the color-developing composition according to any one of (1) to (5).

Figure 1:
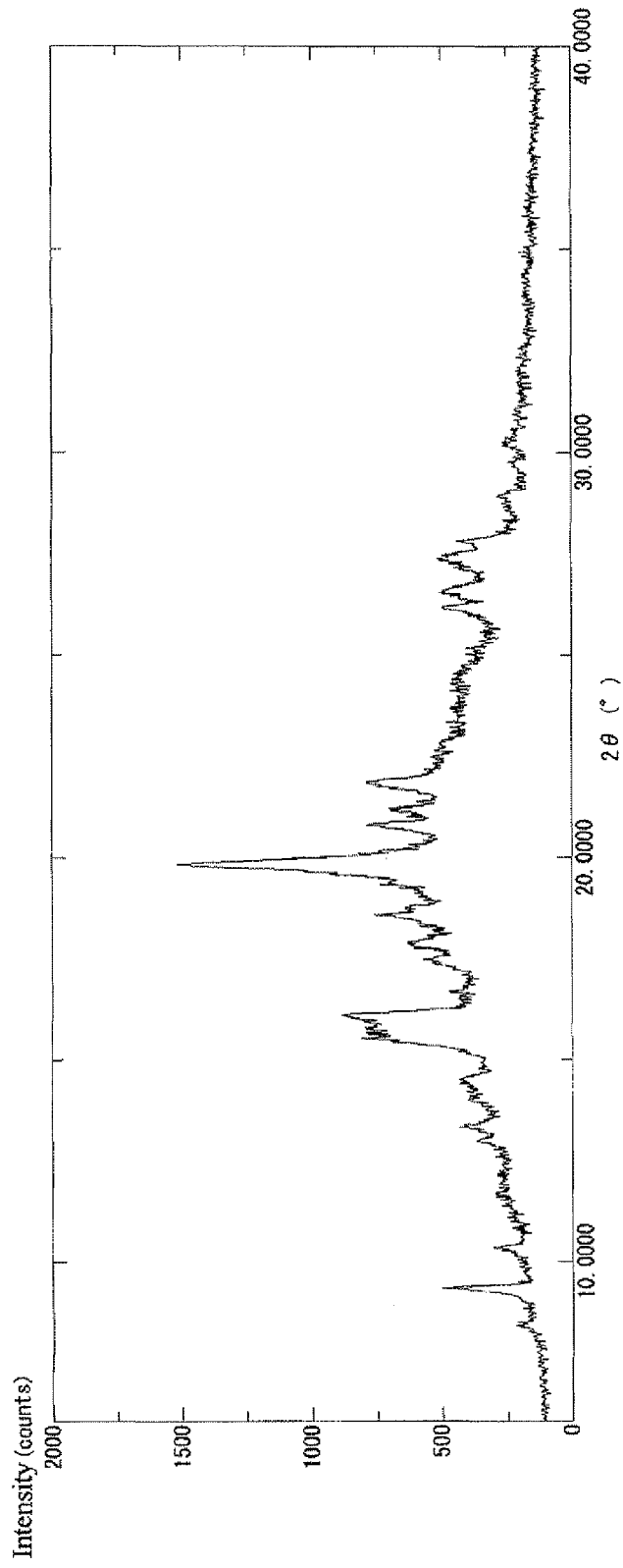
FIG. 1 shows the powder X-ray diffraction pattern of the composition obtained in Synthetic Example 1.

MODE OF CARRYING OUT THE INVENTION (1) Molecular Compound Comprising a Compound Represented by Formula (I) as a Component Compound A molecular compound according to the present invention is a compound wherein two or more types of component compounds that can exist stably on their own are bound by a relatively weak interaction other than a covalent bond represented by a hydrogen bond or Van der Waals' force. Examples of the molecular compound include a hydrate, solvate, adduct and clathrate.

In formula (I), Y represents a C1-C12 hydrocarbon group which is chained or branched and saturated or unsaturated, or a C1-C8 hydrocarbon group which is chained or branched, saturated or unsaturated and has an ether or thioether bond, or represents the following formula

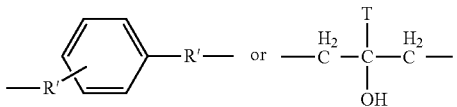

(wherein R's may be the same or different and each represents a methylene group or ethylene group; and T represents a hydrogen atom or a C1-C4 alkyl group).

Examples of the "C1-C12 hydrocarbon group which is chained or branched and saturated or unsaturated" include: an alkylene group such as a methylene group, ethylene group, trimethylene group, tetramethylene group, pentamethylene group, hexamethylene group, heptamethylene group, octamethylene group, nonamethylene group, decamethylene group, undecamethylene group, dodecamethylene group, methylmethylene group, dimethylmethylene group, methylethylene group, ethylethylene group, 1,2-dimethylethylene group, 1-methyltrimethylene group, 1-methyltetramethylene group, 1,3-dimethyltrimethylene group and 1-ethyl-4-methyltetramethylene group; an alkenylene group such as a vinylene group, propenylene group and 2-butenylene group; and an alkynylene group such as an ethynylene group and 2-butynylene group.

Examples of the "C1-C8 hydrocarbon group which is chained or branched, saturated or unsaturated and has an ether or thioether bond" include: a group having an ether bond such as an ethyleneoxyethylene group, tetramethyleneoxytetramethylene group, ethyleneoxyethyleneoxyethylene group, ethyleneoxymethyleneoxyethylene group, 1,3-dioxane-5,5-bismethylene group; and a group having a thioether bond such as an ethylenethioethylene group, tetramethylenethiotetramethylene group, ethylenethioethylenethioethylene group and ethylenethiomethylenethioethylene group.

As for the following formula,

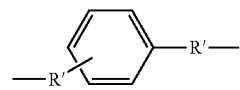

1,2-xylyl group, 1,3-xylyl group and 1,4-xylyl group are exemplified.

As for the following formula,

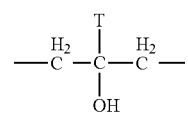

2-hydroxypropylene group, 2-hydroxy-2-methylpropylene group, 2-hydroxy-2-ethylpropylene group, 2-hydroxy-2-propylpropylene group and 2-hydroxy-2-butylpropylene group are exemplified.

$R^1$, $R^2$, $R^3$ and $R^4$ each independently represent a C1-C6 alkyl group or C2-C6 alkenyl group.

Examples of the "C1-C6 alkyl group" include a methyl group, ethyl group, n-propyl group, isopropyl group, n-butyl group, sec-butyl group, tert-butyl group, n-pentyl group, isopentyl group, neopentyl group, tert-pentyl group, n-hexyl group, isohexyl group, 1-methylpentyl group and 2-methylpentyl group.

Examples of the "C2-C6 alkenyl group" include a vinyl group, allyl group, isopropenyl group, 1-propenyl group, 2-butenyl group, 3-butenyl group, 1,3-butanedienyl group and 2-methyl-2-propenyl group.

Preferably, a compound represented by formula (I) is a diphenylsulfone derivative represented by formula (II).

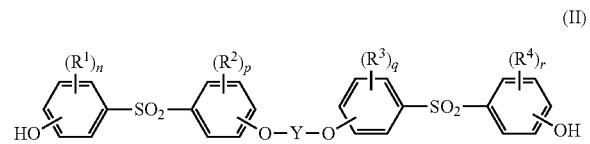

(II)

Particularly preferred is a compound represented by formula (III).

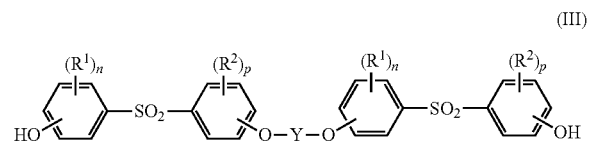

(III)

Further, a compound represented by formula (IV) is advantageous from the synthetic aspect.

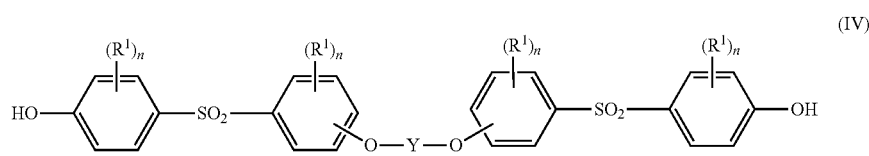

(IV)

Specific examples of the compound represented by formula (I) for use in the present invention include:
bis[4-(4-hydroxyphenylsulfonyl)phenyloxy]methane,
1,2-bis[4-(4-hydroxyphenylsulfonyl)phenyloxy]ethane,
1,3-bis[4-(4-hydroxyphenylsulfonyl)phenyloxy]propane,
1,4-bis[4-(4-hydroxyphenylsulfonyl)phenyloxy]butane,
1,5-bis[4-(4-hydroxyphenylsulfonyl)phenyloxy]pentane,
1,6-bis[4-(4-hydroxyphenylsulfonyl)phenyloxy]hexane,
1,7-bis[4-(4-hydroxyphenylsulfonyl)phenyloxy]heptane,
1,8-bis[4-(4-hydroxyphenylsulfonyl)phenyloxy]octane,
1,9-bis[4-(4-hydroxyphenylsulfonyl)phenyloxy]nonane,
1,10-bis[4-(4-hydroxyphenylsulfonyl)phenyloxy]decane,
1,11-bis[4-(4-hydroxyphenylsulfonyl)phenyloxy]undecane,
1,12-bis[4-(4-hydroxyphenylsulfonyl)phenyloxy]dodecane,
1,1-bis[4-(4-hydroxyphenylsulfonyl)phenyloxy]ethane,
2,2-bis[4-(4-hydroxyphenylsulfonyl)phenyloxy]propane,
1,2-bis[4-(4-hydroxyphenylsulfonyl)phenyloxy]propane,
2,3-bis[4-(4-hydroxyphenylsulfonyl)phenyloxy]propene,
1,2-bis[4-(4-hydroxyphenylsulfonyl)phenyloxy]butane,
2,3-bis[4-(4-hydroxyphenylsulfonyl)phenyloxy]butane,
1,3-bis[4-(4-hydroxyphenylsulfonyl)phenyloxy]butane,
1,4-bis[4-(4-hydroxyphenylsulfonyl)phenyloxy]pentane,
2,4-bis[4-(4-hydroxyphenylsulfonyl)phenyloxy]pentane,
2,5-bis[4-(4-hydroxyphenylsulfonyl)phenyloxy]heptane,
1,2-bis[4-(4-hydroxyphenylsulfonyl)phenyloxy]ethylene,
1,3-bis[4-(4-hydroxyphenylsulfonyl)phenyloxy]propene,
1,4-bis[4-(4-hydroxyphenylsulfonyl)phenyloxy]-2-butene,
1,2-bis[4-(4-hydroxyphenylsulfonyl)phenyloxy]acetylene,
1,4-bis[4-(4-hydroxyphenylsulfonyl)phenyloxy]-2-butyne,
3,4-bis[4-(4-hydroxyphenylsulfonyl)phenyloxy]-1-butene,
2,2'-bis[4-(4-hydroxyphenylsulfonyl)phenyloxy]diethylether,
4,4'-bis[4-(4-hydroxyphenylsulfonyl)phenyloxy]dibutylether,
1,2-bis[4-(4-hydroxyphenylsulfonyl)phenyloxyethyloxy]ethane,
bis[4-(4-hydroxyphenylsulfonyl)phenyloxyethyloxy]methane,
2,2'-bis[4-(4-hydroxyphenylsulfonyl)phenyloxy]diethylthioether,
4,4'-bis[4-(4-hydroxyphenylsulfonyl)phenyloxy]dibutylthioether,
1,2-bis[4-(4-hydroxyphenylsulfonyl)phenyloxyethylthio]ethane,
bis[4-(4-hydroxyphenylsulfonyl)phenyloxyethylthio]methane,
1,4-bis[4-(4-hydroxyphenylsulfonyl)phenyloxymethyl]benzene,
1,3-bis[4-(4-hydroxyphenylsulfonyl)phenyloxymethyl]benzene,
1,2-bis[4-(4-hydroxyphenylsulfonyl)phenyloxymethyl]benzene,
1,3-bis[4-(4-hydroxyphenylsulfonyl)phenyloxy]-2-hydroxypropane,
1,3-bis[4-(4-hydroxyphenylsulfonyl)phenyloxy]-2-methyl-2-hydroxypropane,
1,3-bis[4-(4-hydroxyphenylsulfonyl)phenyloxy]-2-ethyl-2-hydroxypropane,
1,3-bis[4-(4-hydroxyphenylsulfonyl)phenyloxy]-2-propyl-2-hydroxypropane,
1,3-bis[4-(4-hydroxyphenylsulfonyl)phenyloxy]-2-butyl-2-hydroxypropane,
bis[4-(2-hydroxyphenylsulfonyl)phenyloxy]methane,
1,2-bis[4-(2-hydroxyphenylsulfonyl)phenyloxy]ethane,
1,3-bis[4-(2-hydroxyphenylsulfonyl)phenyloxy]propane,
1,4-bis[4-(2-hydroxyphenylsulfonyl)phenyloxy]butane,
1,5-bis[4-(2-hydroxyphenylsulfonyl)phenyloxy]pentane,
1,6-bis[4-(2-hydroxyphenylsulfonyl)phenyloxy]hexane,
1,3-bis[4-(2-hydroxyphenylsulfonyl)phenyloxy]butane,
1,4-bis[4-(2-hydroxyphenylsulfonyl)phenyloxy]-2-butene,
3,4-bis[4-(2-hydroxyphenylsulfonyl)phenyloxy]-1-butene,
2,2'-bis[4-(2-hydroxyphenylsulfonyl)phenyloxy]diethylether,
2,2'-bis[4-(2-hydroxyphenylsulfonyl)phenyloxy]diethylthioether,
1,4-bis[4-(2-hydroxyphenylsulfonyl)phenyloxymethyl]benzene,
1,3-bis[4-(2-hydroxyphenylsulfonyl)phenyloxymethyl]benzene,
1,2-bis[4-(2-hydroxyphenylsulfonyl)phenyloxymethyl]benzene,
1,3-bis[4-(2-hydroxyphenylsulfonyl)phenyloxy]-2-hydroxypropane,
1,3-bis[4-(2-hydroxyphenylsulfonyl)phenyloxy]-2-methyl-2-hydroxypropane,
bis[2-(4-hydroxyphenylsulfonyl)phenyloxy]methane,
1,2-bis[2-(4-hydroxyphenylsulfonyl)phenyloxy]ethane,
1,3-bis[2-(4-hydroxyphenylsulfonyl)phenyloxy]propane,
1,4-bis[2-(4-hydroxyphenylsulfonyl)phenyloxy]butane,
1,5-bis[2-(4-hydroxyphenylsulfonyl)phenyloxy]pentane, 1,6-bis[2-(4-hydroxyphenylsulfonyl)phenyloxy]hexane,
1,3-bis[2-(4-hydroxyphenylsulfonyl)phenyloxy]butane,
1,4-bis[2-(4-hydroxyphenylsulfonyl)phenyloxy]-2-butene,
3,4-bis[2-(4-hydroxyphenylsulfonyl)phenyloxy]-1-butene,
2,2'-bis[2-(4-hydroxyphenylsulfonyl)phenyloxy]diethylether,
2,2'-bis[2-(4-hydroxyphenylsulfonyl)phenyloxy]diethylthioether,
1,4-bis[2-(4-hydroxyphenylsulfonyl)phenyloxymethyl]benzene,
1,3-bis[2-(4-hydroxyphenylsulfonyl)phenyloxymethyl]benzene,
1,2-bis[2-(4-hydroxyphenylsulfonyl)phenyloxymethyl]benzene,
1,3-bis[2-(4-hydroxyphenylsulfonyl)phenyloxy]-2-hydroxypropane,
1,3-bis[2-(4-hydroxyphenylsulfonyl)phenyloxy]-2-methyl-2-hydroxypropane,
2-(4-hydroxyphenylsulfonyl)phenyloxy-4-(2-hydroxyphenylsulfonylphenyloxy)methane,
1-[2-(4-hydroxyphenylsulfonyl)phenyloxy]-2-[4-(2-hydroxyphenylsulfonyl)phenyloxy]ethane,
1-[2-(4-hydroxyphenylsulfonyl)phenyloxy]-3-[4-(2-hydroxyphenylsulfonyl)phenyloxy]propane,
1-[2-(4-hydroxyphenylsulfonyl)phenyloxy]-4-[4-(2-hydroxyphenylsulfonyl)phenyloxy]butane,
1-[2-(4-hydroxyphenylsulfonyl)phenyloxy]-5-[4-(2-hydroxyphenylsulfonyl)phenyloxy]pentane,
1-[2-(4-hydroxyphenylsulfonyl)phenyloxy]-6-[4-(2-hydroxyphenylsulfonyl)phenyloxy]hexane,
1-[2-(4-hydroxyphenylsulfonyl)phenyloxy]-3-[4-(2-hydroxyphenylsulfonyl)phenyloxy]butane,
1-[2-(4-hydroxyphenylsulfonyl)phenyloxy]-4-[4-(2-hydroxyphenylsulfonyl)phenyloxy]-2-butene,
3-[2-(4-hydroxyphenylsulfonyl)phenyloxy]-4-[4-(2-hydroxyphenylsulfonyl)phenyloxy]-1-butene,
2-[2-(4-hydroxyphenylsulfonyl)phenyloxy]-2'-[4-(2-hydroxyphenylsulfonyl)phenyloxy]diethylether,
2-[2-(4-hydroxyphenylsulfonyl)phenyloxy]-2'-[4-(2-hydroxyphenylsulfonyl)phenyloxy]diethylthioether,
1-[2-(4-hydroxyphenylsulfonyl)phenyloxymethyl]-4-[4-(2-hydroxyphenylsulfonyl)phenyloxy]benzene,
1-[2-(4-hydroxyphenylsulfonyl)phenyloxymethyl]-3-[4-(2-hydroxyphenylsulfonyl)phenyloxy]benzene,
1-[2-(4-hydroxyphenylsulfonyl)phenyloxymethyl]-2-[4-(2-hydroxyphenylsulfonyl)phenyloxy]benzene,
1-[2-(4-hydroxyphenylsulfonyl)phenyloxy]-3-[4-(2-hydroxyphenylsulfonyl)phenyloxy]-2-hydroxypropane and
1-[2-(4-hydroxyphenylsulfonyl)phenyloxy]-3-[4-(2-hydroxyphenylsulfonyl)phenyloxy]-2-methyl-2-hydroxypropane.

A compound represented by formula (I) wherein m is 2 can be produced by a double-layer reaction comprising reacting a dihydroxydiphenylsulfone derivative with a dihalogenated alkyl, dihalogenated alkenyl, dihalogenated alkylether, dihalogenated xylene, etc., and reacting a water solvent or water with a water-insoluble organic solvent such as benzene-, ketone- or ester-series solvent in the presence of a basic substance. Dihydroxydiphenylsulfone as a raw material is preferably a 4,4'-dihydroxydiphenylsulfone derivative or a 2,4'-dihydroxydiphenylsulfone derivative for its easy availability. Particularly preferred is 4,4'-dihydroxydiphenylsulfone.

Further, a compound represented by formula (I) may be a sole compound represented by formula (I) or a combination of two or more types of compounds represented by formula (I). A mixture containing a compound represented by formula (I) may also be used. For instance, a product may also be used that contains, as a main component, a compound of formula (I') which is obtained through the reaction of 4,4'-dihydroxydiphenylsulfone and 2,2'-dichlorodiethylether. This product comprises 2,2'-bis[4-(4-hydroxyphenylsulfonyl)phenyloxy]diethylether (the n=1 compound in formula (I')) which is a compound represented by formula (I).

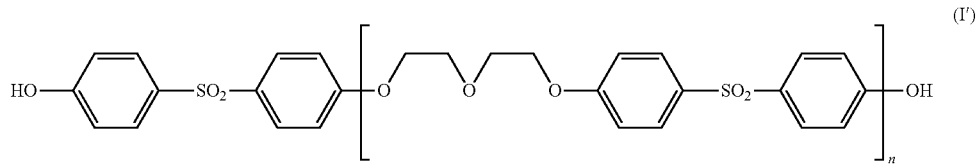

(I')

(wherein n represents any integer of 1 to 6)

This reaction composition is consisted of a mixture of reaction products with different polymerization degrees, and it is preferred that the reaction composition contains all of the compounds from n=1 to n=6 represented by formula (I'). However, because the production ratios differ among these compounds depending on reaction conditions and the like, it suffices if at least one type of compounds is contained as for the compounds where n is 2 or more. Preferably, a compound of n=1 is contained by 5-80% by mass, preferably 10-60% by mass, particularly preferably 20-50% by mass relative to the solid content of the reaction composition.

A compound represented by formula (I) for use in the present invention is usually crystal and sometimes amorphous or liquid. In addition, a compound represented by formula (I) may be a crystalline polymorph. These compounds, regardless of the forms, all belong to the present invention as a compound represented by formula (I).

In the present invention, a substance which forms a molecular compound together with a compound represented by formula (I) is not particularly limited as long as it is capable of forming a molecular compound with the compound represented by formula (I) and which can be used as a recording material. Specific examples include: water, alcohols such as methanol, ethanol, isopropanol, n-butanol, n-octanol, 2-ethylhexanol, allylalcohol, propargylalcohol, 1,2-butanediol, 1,3-butanediol, 1,4-butanediol, cyclohexanediol, 2-bromo-2-nitropropane-1,3-diol, 2,2-dibromo-2-nitroethanol and 4-chlorophenyl-3-iodinepropargylformal; aldehydes such as formaldehyde, acetoaldehyde, n-butylaldehyde, propionaldehyde, benzaldehyde, phthalaldehyde, α-bromcinnamaldehyde and phenylacetoaldehyde; ketones such as acetone, methylethylketone, diethylketone, dibutylketone, methylisobutylketone, cyclohexanone, acetylacetone and 2-bromo-4'-hydroxyacetophenone; nitriles such as acetonitrile, acrylonitrile, n-butylonitrile, malononitrile, phenylacetonitrile, benzonitrile, cyanopyridine, 2,2-dibromomethylglutarnitrile, 2,3,5,6-tetrachloroisophthalonitrile, 5-chloro-2, 4,6-trifluoroisophthalonitrile and 1,2-dibromo-2,4-dicyanobutane; ethers such as diethylether, dibutylether, tetrahydrofuran, dioxane, tetrahydropyran, dioxolan and trioxane; esters such as methyl acetate, ethyl acetate, butyl acetate, n-heptylacetate and bis-1,4-bromoacetoxy-2-butene; sulfonamides such as benzenesulfonamide; amides such as N-methylformamide, N,N-dimethylformamide, dicyandiamide, dibromnitrilepropionamide, 2,2-dibromo-3-nitrilopropionamide and N,N-diethyl-m-toluamide; halogenated hydrocarbons such as dichloromethane, chloroform, dichloroethylene and tetrachloroethylene; lactams such as ϵ-caprolactam; lactones such as ϵ-caprolactone; oxiranes such as aryiglycidylether; morpholines; phenols such as phenol, cresol, resorcinol and p-chloro-m-cresol; carboxylic acids and thiocarboxylic acids such as formic acid, acetic acid, propionic acid, oxalic acid, citric acid, adipic acid, tartaric acid, benzoic acid, phthalic acid and salicylic acid; sulfamic acids; thiocarbamic acids; thiosemicarbazides; urea and thioureas such as urea, phenylurea, diphenylurea, thiourea, phenylthiourea, diphenylthiourea and N,N-dimethyldichlorophenylurea; isothioureas; sulfonylureas; thiols such as thiophenol, allylmercaptan, n-butylmercaptan and benzylmercaptan; sulfides such as benzylsulfide and butylmethylsulfide; disulfides such as dibutyldisulfide, dibenzyldisulfide and tetramethylthiuramdisulfide; sulfoxides such as dimethylsulfoxide, dibutylsulfoxide and dibenzylsulfoxide; sulfones such as dimethylsulfone, phenylsulfone, phenyl-(2-cyano-2-chlorovinyl)sulfone, hexabromodimethylsulfone and di-iodomethyl-para-tolylsulfone; thiocyanic acids and isothiocyanic acids such as thiocyanic acid methyl ester and isothiocyanic acid methyl ester; amino acids such as glycine, alanine, leucine, lysine, methionine and glutamine; amide and urethane compounds; acid anhydrides; aromatic hydrocarbons such as benzene, toluene and xylene; alkanes; alkenes; alkynes; isocyanates such as butylisocyanate, cyclohexylisocyanate and phenylisocyanate; thiocyanates and isothiocyanates such as methylenebisthiocyanate and methylenebisisothiocyanate; nitro compounds such as tris(hydroxymethyl)nitromethane; acyclic aliphatic amines such as ammonia, methylamine, ethylamine, propylamine, butylamine, pentylamine, hexylamine, allylamine, hydroxylamine, ethanolamine, benzylamine, ethylenediamine, 1,2-propanediamine, 1,3-propanediamine, 1,4-butanediamine, 1,5-pentanediamine, 1,6-hexanediamine, diethylenetriamine, triethylenetetramine, tetraethylenepentamine, dipropylenediamine, N,N-dimethylethylenediamine, N,N'-dimethylethylenediamine, N,N-dimethyl-1,3-propanediamine, N-ethyl-1,3-propanediamine, trimethylhexamethylenediamine, alkyl-t-monoamine, menthanediamine, isophoronediamine, guanidine, N-(2-hydroxypropyl)aminomethanol; cyclohexylamine; cyclohexanediamine; bis(4-aminocyclohexyl)methane; pyrrolidines; azetidines; piperidines; piperazines such as piperazine, N-aminoethylpiperazine and N,N'-dimethylpiperazine; cyclic aliphatic amines such as pyrrolines; aromatic amines such as aniline, N-methylaniline, N,N-dimethylaniline, o-phenylenediamine, m-phenylenediamine, p-phenylenediamine, diaminodiphenylmethane, diaminodiphenylsulfone and m-kylenediamine; modified polyamines such as an epoxy compound addition polyamine, Michael addition polyamine, Mannich addition polyamine, thiourea addition polyamine and ketone blocking polyamine; imidazoles such as imidazole, 2-methylimidazole, 2-ethylimidazole, 2-isopropylimidazole, 2-n-propylimidazole, 2-ethyl-4-methylimidazole, 1-benzyl-2-methylimidazole, 2-undecyl-1H-imidazole, 2-heptadecyl-1H-imidazole, 2-phenyl-1H-imidazole, 4-methyl-2-phenyl-1H-imidazole and 1-benzyl-2-methylimidazole; a nitrogen-containing heterocyclic compound such as pyrrole, pyridine, picoline, pyrazine, pyridazine, pyrimidine, pyrazole, triazole, benzotriazole, triazine, tetrazole, purine, indole, quinoline, isoquinoline, carbazole, imidazoline, pyrroline, oxazole, piperine, pyrimidine, pyridazine, benzimidazole, indazole, quinazoline, quinoxaline, phthalimide, adenine, cytosine, guanine, uracil, 2-methoxycarbonylbenzimidazole, 2,3,5,6-tetrachloro-4-methanesulfonylpyridine, 2,2-dithio-bis-(pyridine-1-oxide), N-methylpyrrolidone, 2-benzimidazolemethylcarbamate, 2-pyridinethiol-1-oxide sodium, hexahydro-1,3,5-tris(2-hydroxyethyl)-s-triazine, hexahydro-1,3,5-triethyl-s-triazine, 2-methylthio-4-t-butylaminio-6-cyclopropylamino-s-triazine, N-(fluorodichloromethylthio) phthalimide, 1-bromo-3-chloro-5,5-dimethylhydantoin, 2-methoxycarbonylbenzimidazole and 2,4,6-trichlorophenylmaleimide; an oxygen-containing heterocyclic compound such as furan, furfurylalcohol, tetrahydrofurfurylalcohol, furfurylamine, pyran, coumarin, benzofuran, xanthene and benzodioxane; a nitrogen- and oxygen-containing heterocyclic compound such as oxazole, isoxazole, benzoxazole, benzoisoxazole, 5-methyloxazolidine, 4-(2-nitrobutyl)morpholine and 4,4'-(2-ethyl-2-nitrotrimethylene)dimorpholine; a sulfur-containing heterocyclic compound such as thiophene, 3,3,4,4-tetrahydrothiophene-1,1-dioxide, 4,5-dichloro-1,2-dithioran-3-one, 5-chloro-4-phenyl-1,2-dithioran-3-one and 3,3,4,4-tetrachlorotetrahydrothiophene-1,1-dioxide; a nitrogen- and sulfur-containing heterocyclic compound such as thiazole, benzothiazole, 5-chloro-2-methyl-4-isothiazoline-3-one, 2-methyl-4-isothiazoline-3-one, 4,5-dichloro-3-n-octylisothiazoline-3-one, 2-octyl-4-isothiazoline-3-one, 1,2-benzisothiazoline-3-one, 2-thiocyanomethylbenzothiazole, 2-(4-thiazoryl)benzimidazole and 2-thiocyanomethylbenzothiazole; steroids such as cholesterol; alkaloids such as brucine, kinin and theophylline; natural essential oils such as cineol, hinokitiol, menthol, terpineol, borneol, nopol, citral, citronellol, citronellal, geraniol, menthone, eugenol, linalool and dimethyloctanol; synthetic perfumes such as fragrant olive, jasmine and lemon; vitamins and related compounds such as ascorbic acid, nicotinic acid and nicotinic acid amide. Particularly preferred are water, methanol and 1,4-dioxane.

A molecular compound for use in the present invention can be obtained by mixing, either directly or in a solvent, a compound represented by formula (I) or a mixture thereof with the above-mentioned substance which forms a molecular compound together with the compound represented by formula (I) and the like. When the substance has a low boiling point or a high vapor pressure, a target molecular compound can be obtained by applying vapor of such substance to a compound represented by formula (I). Further, a target molecular compound can be obtained by first generating a molecular compound consisting of a compound represented by formula (I) and a certain substance, followed by reacting this molecular compound with a target component compound by a method described above.

A molecular compound for use in the present invention can also be generated during the course of production of a compound represented by formula (I) or a mixture thereof.

For example, in a case where 4,4'-dihydroxydiphenylsulfone and 2,2'-dichlorodiethylether are reacted to produce a mixture comprising 2,2'-bis[4-(4-hydroxyphenylsulfonyl)phenyloxy]diethylether, a mixture containing such molecular compound can be obtained by causing contact, during the production process, with a compound which can form a molecular compound together with 2,2'-bis[4-(4-hydroxyphenylsulfonyl)phenyloxy]diethylether.

That a molecular compound has been generated can be confirmed by thermal analysis (TG and DTA), infrared absorption spectra (IR), X-ray diffraction pattern, solid NMR spectra, etc. In addition, the compositional ratio of the molecular compound can be confirmed by thermal analysis, $^1$HNMR spectra, high performance liquid chromatography (HPLC), elementary analysis, etc.

The ratio of component compounds that constitute a molecular compound for use in the present invention may vary depending on the condition for generating the molecular compound. Further, a molecular compound consisting of three or more multiple components can also be obtained by allowing two or more kinds of substances to react with a compound represented by formula (I).

It is preferred that a molecular compound for use in the present invention is crystalline. When such is the case, even the same molecular compounds sometimes take a crystalline polymorph. Crystallinity can be confirmed mainly by determining an X-ray diffraction pattern. Also, presence of the crystalline polymorph can be confirmed by thermal analysis, X-ray diffraction pattern, solid NMR, etc.

(2) Color-Developing Composition

A color-developing composition containing a molecular compound comprising a compound represented by formula (I) as a component compound may be consisted of such molecular compound only or may be consisted by comprising other compounds than such molecular compound.

(3) Recording Material

A color-developing composition of the present invention may be used as a thermal recording material in a similar manner to when using known image storage stabilizers or color-developing agents. For example, a recording material can be produced as follows. Suspension solutions are mixed and applied onto a support, such as a paper, and dried, wherein the suspension solutions are prepared by respectively dispersing microparticles of a color-developing composition of the present invention and microparticles of a color-forming compound in the aqueous solutions comprising a water-soluble binder such as polyvinylalcohol and cellulose. Further, apart from the methods as described above wherein the color-developing composition is contained in the color-forming layer, the color-developing composition can also be contained in any layer such as a protection layer, undercoating layer, etc. in case of a multi-layer structure.

The ratio of a color-developing composition of the present invention to be used for a color-forming compound is 0.01 to 100 parts by mass relative to 1 part by mass of the color-forming compound. When used as a color-developing adjuvant, the ratio is preferably 0.01 to 10 parts by mass and particularly preferably 0.2 to 5 parts by mass relative to 1 part by mass of the color-forming compound. When used as a color-developing agent, the ratio is preferably 1 to 10 parts by mass, particularly preferably 1.5 to 5 parts by mass relative to 1 part by mass of the color-forming compound.

Two or more types of molecular compounds comprising a compound represented by formula (I) as a component compound may be used as a color-developing composition for a recording material of the present invention. For example, among the color-developing compositions of the present invention, one may be used as an image storage stabilizer and another as a color-developing agent. A mixture of the two or more types can be prepared by mixing the color-developing compositions in advance or they may be mixed at the point of use. In addition, a color-developing composition may be mixed with a color-forming compound or the like in such a manner that the compositions are mixed as powder, or added at the point of the preparation and dispersion of the application solution, or added in the form of a dispersion solution. Particularly, it is considerably effective when using a color-developing composition of the present invention as a color-developing agent.

Further, a molecular compound comprising a compound represented by formula (I) as a component compound have different crystalline forms depending on the conditions for precipitating crystals such as solvent types and the precipitation temperature, where all of these belong to the present invention as the molecular compound. These molecular compounds can be demonstrated based on the melting point of the crystal, an infrared spectroscopic analysis, X-ray diffraction analysis, etc.

A recording material of the present invention may further contain as necessary one or more of the following: another color-developing agent, another image storage stabilizer, sensitizer, filler, dispersant, antioxidant, desensitizer, antiadhesive agent, defoamer, light stabilizer, fluorescent brightener, etc. These are respectively used in an amount of usually within a range of 0.01 to 15 parts by mass, preferably 1 to 10 parts by mass, relative to 1 part by mass of the color-forming compound. These agents may be contained in the color-forming layer, while they may be contained in any layer such as a protective layer when the recording material consists of a multilayer structure. Especially when an overcoat layer or undercoat layer is provided on the upper part and/or the bottom part of the color-forming layer, such overcoat layer and undercoat layer may contain an antioxidant, light stabilizer, etc. In addition, an antioxidant and a light stabilizer may be contained in these layers. Further, an antioxidant and a light stabilizer can be contained in these layers in such a manner as being encapsulated in a microcapsule according to need.

When a color-developing composition of the present invention is used in combination with other color-developing agent, examples of such color-developing agent to be used include the following and they may be used alone or in combination of two or more kinds thereof according to need: a bisphenol compound such as bisphenol A, 4,4'-sec-butylidenebisphenol, 4,4'-cyclohexylidenebisphenol,
2,2'-bis(4-hydroxyphenyl)-3,3'-dimethylbutane,
2,2'-dihydroxydiphenyl,
pentamethylene-bis(4-hydroxybenzoate),
2,2'-dimethyl-3,3'-di(4-hydroxyphenyl)pentane,
2,2'-di(4-dihydroxyphenyl)hexane,
2,2-bis(4-hydroxyphenyl)propane,
2,2-bis(4-hydroxyphenyl)butane,
2,2-bis(4-hydroxy-3-methylphenyl)propane,
4,4'-(1-phenylethylidene)bisphenol,
4,4'-ethylidenebisphenol, (hydroxyphenyl)methylphenol,
2,2-bis(4-hydroxyphenyl)-4-methylpentane,
4,4-isopropylidenebis-o-cresol,
4,4'-dihydroxy-diphenylmethane,
2,2'-bis(4-hydroxy-3-phenyl-phenyl)propane,
4,4'-(1,3-phenylenediisopropylidene)bisphenol,
4,4'-(1,4-phenylenediisopropylidene)bisphenol, and
2,2-bis(4-hydroxyphenyl)butyl acetate; a sulfur containing bisphenol such as 4,4'-dihydroxydiphenylthioether,
1,7-di(4-hydroxyphenylthio)-3,5-dioxaheptane,
2,2'-di(4-hydroxyphenylthio)diethylether,
4,4'-dihydroxy-3,3'-dimethylphenylthioether, 1,5-di(4-hydroxyphenylthio)-3-oxapentane,
bis(4-hydroxyphenylthioethoxy)methane, and a condensation mixture primarily comprising a binuclear condensate of 2,2'-methylenebis(4-t-butylphenol) described in Japanese Laid-Open Patent Application No. 2003-154760;
4'-hydroxy-4-methylbenzenesulfonanilide;
4,4'-bis((4-methyl-3-phenoxycarbonyl)aminophenylureide)) diphenylsulfone; 3-(3-phenylureide)benzenesulfonamide; octadecyl phosphate; and a diphenylsulfone cross-linking compound represented by the following formula (I') and the mixtures thereof.

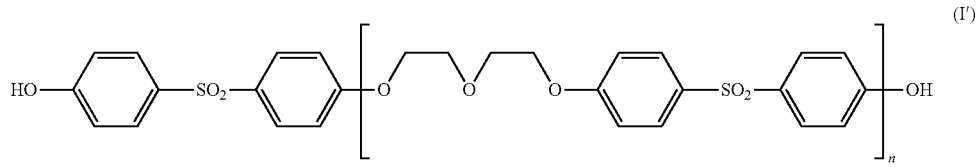

(I')

(wherein n represents any integer 1 to 6)

Preferably exemplified are 4,4'-isopropylidenediphenol,
2,2-bis(4-hydroxyphenyl)-4-methylpentane,
4,4'-isopropylidenebis-o-cresol,
4,4'-(1-phenylethylidene)bisphenol,
4,4'-cyclohexylidenebisphenol,
2,2-bis(4-hydroxy-3-phenyl-phenyl)propane,
4,4'-(1,3-phenylendiisopropylidene)bisphenol,
4,4'-(1,4-phenylendiisopropylidene)bisphenol,
bis(p-hydroxyphenyl)butyl acetate,
4,4'-dihydroxydiphenylsulfone,
2,4'-dihydroxydiphenylsulfone,
bis(3-allyl-4-hydroxyphenyl)sulfone,
4-hydroxy-4'-isopropoxydiphenylsulfone,
4-hydroxy-4'-n-propoxydiphenylsulfone,
4-hydroxy-4'-allyloxydiphenylsulfone,
4-hydroxy-4'-benzyloxydiphenylsulfone,
3,4-dihydroxyphenyl-4'-methylphenylsulfone,
N-(2-hydroxyphenyl)-2-[(4-hydroxyphenyl)thio]acetamide,
N-(4-hydroxyphenyl)-2-[(4-hydroxyphenyl)thio]acetamide,
an equivalent mixture of
N-(2-hydroxyphenyl)-2-[(4-hydroxyphenyl)thio]acetamide and
N-(4-hydroxyphenyl)-2-[(4-hydroxyphenyl)thio]acetamide,
benzyl p-hydroxybenzoate,
di(4-hydroxy-3-methylphenyl)sulfide, 4-hydroxybenzene sulfonanilide, hydroquinonemonobenzyl ether, a condensation mixture primarily comprising a binuclear condensate of 2,2'-methylenebis(4-t-butylphenol) described in Japanese Laid-Open Patent Application No. 2003-154760, 4,4'-bis(N-p-tolylsulfonylaminocarbonylamino)diphenylmethane, N-p-tolylsulfonyl-N'-3-(p-tolylsulfonyloxy) phenylurea, 4,4'-bis[(4-methyl-3-phenoxycarbonylaminophenylureide)]diphenylsulfone, 3-(3-phenylureide) benzenesulfonamide, zinc-bis[4-(n-octyloxycarbonylamino)salicylate]dihydrate, zinc 4-[2-(4-methoxyphenoxy)ethoxy]salicylate and zinc 3,5-bis(α-methylbenzyl)salicylate.

More specifically, these color-developing agents may be appropriately used at a ratio of such as 0.1 to 10 parts by mass relative to 1 part by mass of a color-developing composition of the present invention. For example, a thermal recording paper can be produced by combining 1 part by mass of a color-developing composition of the present invention and 1 part by mass of 4-hydroxy-4'-isopropoxydiphenylsulfone as other color-developing agent, relative to 1 part by mass of 3-di(n-butyl)amino-6-methyl-7-anilinofluoran as a dye. Likewise, the color-developing agents referred to above such as 4-hydroxy-4'-n-propoxydiphenylsulfone, 4-hydroxy-4'-allyloxydiphenylsulfone and 2,4'-dihydroxydiphenylsulfone may be combined.

Following color-developing agents are also exemplified when used for pressure sensitive copying papers: an inorganic acid substance such as an acid earth, activated earth, attapulgite, bentonite, colloidal silica, aluminum silicate, magnesium silicate, zinc silicate, tin silicate, fired kaolin and talc; aliphatic carboxylic acid such as oxalic acid, maleic acid, tartaric acid, citric acid, succinic acid and stearic acid; aromatic carboxylic acid such as benzoic acid, p-t-butylbenzoic acid, phthalic acid, gallic acid, salicylic acid, 3-isopropylsalicylic acid, 3-phenylsalicylic acid, 3-cyclohexylsalicylic acid, 3-5-di-t-butylsalicylic acid, 3-methyl-5-benzylsalicylic acid, 3-phenyl-5-(2,2-dimethylbenzyl)salicylic acid, 3,5-di-(2-methylbenzyl)salicylic acid and 2-hydroxy-1-benzyl-3-naphthoic acid; a metallic salt such as zinc, magnesium, aluminum and titanium of these aromatic carboxylic acids; a color-developing agent based on phenolic resin such as p-phenylphenol-formalin resin and p-butylphenol-acetylene resin; and a mixture of such phenolic resin-based color-developing agent and the metallic salt of an aromatic carboxylic acid mentioned above.

When using a color-developing composition comprising a molecular compound, which contains a compound represented by formula (I), and other color-developing agent in combination, content of the composition is not particularly restricted. However, the mass ratio of the composition and other color-developing agent is preferably within a range of 10:0.01 to 0.01:10, more preferably within a range of 10:0.1 to 0.1:10, and still more preferably within a range of 10:1 to 1:10.

Examples of the color-forming compound to be used for a recording material of the present invention include: a leuco dye such as fluoran-based, phthalide-based, lactam-based, triphenylmethane-based, phenothiazine-based and spiropyran-based dyes. The color-forming compound, however, is not limited to these examples and any color-forming compound may be used as long as it forms color by contacting with an acid substance. Further, although it is a matter of course to use these color-forming compounds singularly to produce a recording material of the color developed by the dye used, the color-forming compounds may also be used in combination of two or more kinds thereof. For example, it is possible to produce a recording material that produces a real black by using dyes developing three primary colors (red, blue, green) and/or black dyes in combination.

Examples of the color-forming compound include:
3-diethylamino-6-methyl-7-anilinofluoran,
3-di(n-butyl)amino-6-methyl-7-anilinofluoran,
3-(N-methyl-N-cyclohexylamino)-6-methyl-7-anilinofluoran,
3-(N-ethyl-N-isobutylamino)-6-methyl-7-anilinofluoran,
3-(N-methyl-N-propylamino)-6-methyl-7-anilinofluoran,
3-(N-ethyl-N-isoamylamino)-6-methyl-7-anilinofluoran,
3-(N-ethyl-p-toluidino)-6-methyl-7-anilinofluoran,
3-diethylamino-7-(m-trifluoromethylanilino)fluoran,
3-di(n-pentyl)amino-6-methyl-7-anilinofluoran,
3-(N-ethyl-N-ethoxypropylamino)-6-methyl-7-anilinofluoran,
3-diethylamino-6-methyl-7-n-octylaminofluoran,
3-diethylamino-6-methyl-7-(m-methylanilino)fluoran,
3-diethylamino-6-methyl-7-(o,p-dimethylanilino)fluoran,
3-diethylamino-6-chloro-7-anilinofluoran,
3-diethylamino-7-(o-chloroanilino)fluoran,
3-dibutylamino-7-(o-chloroanilino)fluoran,
3-(N-ethyl-N-tetrahydrofurfurylamino)-6-methyl-7-anilinofluoran,
3-dibutylamino-7-(o-fluoroanilino)fluoran,
3-diethylamino-7-(o-fluoroanilino)fluoran,
2,4-dimethyl-6-[(4-dimethylamino)anilino]fluoran,
2-chloro-3-methyl-6-p(p-phenylaminophenyl)aminoanilinofluoran,
3,3-bis[1-(4-methoxyphenyl)-1-(4-dimethylaminophenyl)ethylene-2-yl]-4,5,6,7-tetrachlorophthalide,
3,6,6'-tris(dimethylamino)spiro[fluorene-9,3'-phthalide],
3,3-bis(p-dimethylaminophenyl)-6-dimethylaminophthalide,
10-benzoyl-3,7-bis(dimethylamino)phenothiazine,
3-(4-diethylamino-2-hexyloxyphenyl)-3-(1-ethyl-2-methyl-3-indolyl)-4-azaphthalide,
3-(4-diethylamino-2-methylphenyl)-3-(1-ethyl-2-methyl-3-indolyl)-4-azaphthalide,
3-(4-diethylamino-2-ethoxyphenyl)-3-(1-ethyl-2-methyl-3-indolyl)-4-azaphthalide,
3-(4-diethylamino-2-ethoxyphenyl)-3-(1-octyl-2-methyl-3-indolyl)-4-azaphthalide,
3-diethylamino-5-methyl-7-dibenzylaminofluoran,
3-diethylamino-7-dibenzylaminofluoran, 3-(N-ethyl-p-tolyl)amino-7-N-methylanilinofluoran,
3,3-bis(4-diethylamino-2-ethoxyphenyl)-4-azaphthalide,
3-[2,2-bis(1-ethyl-2-methylindole-3-yl)vinyl]-3-[4-(diethylamino)phenyl]isobenzofuran-1-one,
3,6,6'-tris(dimethylamino)spiro[fluorene-9,3'-phthalide],
2-[3,6-bis(diethylamino)-9-(o-chloroanilino)xanthyl]benzoic acid lactam, 3-diethylamino-7-chlorofluoran,
3,6-bis-(diethylamino)fluoran-γ-(4'-nitro)-anilinolactam,
3-diethylamino-benzo[a]fluoran,
3-(N-ethyl-N-isopentylamino)-benzo[a]fluoran,
2-methyl-6-(N-ethyl-N-p-tolylamino)fluoran,
3,3-bis(1-butyl-2-methyl-3-indolyl)phthalide,
3-diethylamino-6-methyl-7-chlorofluoran,
3-dibutylamino-6-methyl-7-bromofluoran,
3-cyclohexylamino-6-chlorofluoran,
3-diethylamino-6,8-dimethylfluoran and
4,4'-isopropylidenedi(4-phenoxy)bis[4-(quinazoline-2-yl)-N,N-diethylaniline].

Preferred examples of the black dye include:
3-diethylamino-6-methyl-7-anilinofluoran,
3-di(n-butyl)amino-6-methyl-7-anilinofluoran,
3-(N-methyl-N-cyclohexylamino)-6-methyl-7-anilinofluoran,
3-(N-methyl-N-propylamino)-6-methyl-7-anilinofluoran,
3-(N-ethyl-N-isoamylamino)-6-methyl-7-anilinofluoran,
3-(N-ethyl-p-toluidino)-6-methyl-7-anilinofluoran,
3-diethylamino-7-(m-trifluoromethylanilino)fluoran,
3-di(n-pentyl)amino-6-methyl-7-anilinofluoran,
3-(N-ethyl-N-ethoxypropylamino)-6-methyl-7-anilinofluoran,
3-diethylamino-6-methyl-7-n-octylaminofluoran,
3-diethylamino-6-methyl-7-(m-methylanilino)fluoran,
3-diethylamino-6-chloro-7-anilinofluoran,
3-diethylamino-7-(o-chloroanilino)fluoran,
3-dibutylamino-7-(o-chloroanilino)fluoran,
3-(N-ethyl-N-tetrahydrofurfurylamino)-6-methyl-7-anilinofluoran and 3-dibutylamino-7-(o-fluoroanilino)fluoran.

Especially preferred examples include:
3-diethylamino-6-methyl-7-anilinofluoran,
3-di(n-butyl)amino-6-methyl-7-anilinofluoran,
3-(N-ethyl-N-isoamylamino)-6-methyl-7-anilinofluoran,
3-(N-ethyl-p-toluidino)-6-methyl-7-anilinofluoran and
3-di(n-pentyl)amino-6-methyl-7-anilinofluoran.

The near-infrared absorption dye can be exemplified by 3,3-bis[1-(4-methoxyphenyl)-1-(4-dimethylaminophenyl)ethylene-2-yl]-4,5,6,7-tetrachlorophthalide and 3,6,6'-tris(dimethylamino)spiro[fluorene-9,3'-phthalide].

In addition, examples of the blue dye, green dye, red dye and yellow dye include:

3,3-bis(p-dimethylaminophenyl)-6-dimethylaminophthalide,
3-(4-diethylamino-2-ethoxyphenyl)-3-(1-ethyl-2-methyl-3-indolyl)-4-azaphthalide,
3-(4-diethylamino-2-ethoxyphenyl)-3-(1-octyl-2-methyl-3-indolyl)-4-azaphthalide, 3-diethylamino-7-dibenzylaminofluoran,
3-(N-ethyl-p-tolyl)amino-7-N-methylanilinofluoran,
3,3-bis(4-diethylamino-2-ethoxyphenyl)-4-azaphthalide,
3,6,6'-tris(dimethylamino)spiro[fluorene-9,3'-phthalide],
3-diethylamino-7-chlorofluoran,
3-diethylamino-benzo[a]fluoran,
3-diethylamino-6-methyl-7-chlorofluoran,
3-cyclohexylamino-6-chlorofluoran,
3-diethylamino-6,8-dimethylfluoran and
4,4'-isopropylidenedi(4-phenoxy)bis[4-(quinazoline-2-yl)-N,N-diethylaniline].

When a color-developing composition of the present invention is used in combination with other image storage stabilizer, the examples of such image storage stabilizer include the following and they may be used alone or in combination of two or more kinds thereof according to need:
1,1,3-tris(2-methyl-4-hydroxy-5-t-butylphenyl)butane,
1,1,3-tris(2-methyl-4-hydroxy-5-t-cyclohexylphenyl)butane,
4,4'-butylidenebis(6-t-butyl-3-methylphenol),
2,2'-methylenebis(6-t-butyl-4-methylphehol),
2,2'-methylenebis(6-t-butyl-4-ethylphenol),
4,4'-thiobis(6-t-butyl-3-methylphenol),
1,3,5-tris(2,6-dimethyl-4-t-butyl-3-hydroxybenzyl)isocyanurate,
1,3,5-tris[[3,5-bis(1,1-dimethylethyl)-4-hydroxyphenyl]methyl]-1,3,5-triazine-2,4,6(1H,3H,5H)-trione,
2-methyl-2-[[4-[[4-(phenylmethoxy)phenyl]sulfonyl]phenoxy]methyl]-oxirane,
2,4,8,10-(tetra(t-butyl)-6-hydroxy-12H-dibenzo[d,g][1,3,2]dioxaphosphocin-6-oxide sodium salt,
2,2-bis(4'-hydroxy-3',5'-dibromophenyl)propane,
4,4'-sulfonylbis(2,6-dibromophenol)
2-(2'-hydroxy-5'-methylphenyl)benzotriazole,
4-benzyloxy-4-(2-methylglycidyloxy)-diphenylsulfone,
4,4'-diglycidyloxydiphenylsulfone, 1,4-diglycidyloxybenzene,
4-(α-(hydroxymethyl)benzyloxy)-4'-hydroxydiphenylsulfone
and 2,2-methylenebis(4,6-tert-butylphenyl)phosphate.

Preferably exemplified are
1,1,3-tris(2-methyl-4-hydroxy-5-t-butylphenyl)butane,
1,1,3-tris(2-methyl-4-hydroxy-5-t-cyclohexylphenyl)butane,
4,4'-butylidenebis(6-t-butyl-3-methylphenol),
2,2'-methylenebis(4-ethyl-6-t-butylphenol),
1,3,5-tris(2,6-dimethyl-4-t-butyl-3-hydroxybenzyl) isocyanurate,
2-methyl-2-[[4-[[4-(phenylmethoxy)phenyl]sulfonyl]phenoxy]methyl]-oxirane, 4,4'-sulfonylbis(2,6-dibromophenol) and
2-(2'-hydroxy-5'-methylphenyl)benzotriazole.

Examples of the sensitizer include the following and they may be used alone or in combination of two or more kinds thereof according to need: a higher fatty acid amide such as stearic acid amide; benzamide; stearic acid anilide; acetoacetanilide; thioacetanilide; dibenzyl oxalate; di(4-methylbenzyl)oxalate; di(4-chlorobenzyl)oxalate; dimethyl phthalate; dimethyl terephthalate; dibenzyl terephthalate; dibenzyl isophthalate; bis(tert-butylphenol); diphenylsulfone and its derivative such as 4,4'-dimethoxydiphenylsulfone, 4,4'-diethoxydiphenylsulfone,
4,4'-dipropoxydiphenylsulfone,
4,4'-diisopropoxydiphenylsulfone,
4,4'-dibutoxydiphenylsulfone,
4,4'-diisobutoxydiphenylsulfone,
4,4'-dipentyloxydiphenylsulfone, 4,4'-dihexylphenylsulfone,
2,4'-dimethoxydiphenylsulfone, 2,4'-diethoxydiphenylsulfone,
2,4'-dipropoxydiphenylsulfone,
2,4'-diisopropoxydiphenylsulfone,
2,4'-dibutoxydiphenylsulfone,
2,4'-dipentyloxydiphenylsulfone,
2,4'-dihexyloxydiphenylsulfone; diethers of
4,4'-dihydroxydiphenylsulfone; diethers of 2,4'-dihydroxydiphenylsulfone; 1,2-bis(phenoxy)ethane;
1,2-bis(4-methylphenoxy)ethane;
1,2-bis(3-methylphenoxy)ethane; diphenylamine; carbazole;
2,3-di-m-tolylbutane; 4-benzylbiphenyl;
4,4'-dimethylbiphenyl; m-terphenyl;
di-β-naphthylphenylenediamine; 1-hydroxy-2-naphthoic acid phenyl ester; 2-naphthylbenzyl ether;
4-methylphenyl-biphenylether;
1,2-bis(3,4-dimethylphenyl)ethane;
2,3,5,6-tetramethyl-4'-methyldiphenylmethane;
1,2-bis(phenoxymethyl)benzene; acrylic acid amide;
diphenylsulfone; 4-acetylbiphenyl; and carbonic acid diphenyl.

Preferably exemplified are 2-naphthylbenzylether, m-terphenyl, p-benzylbiphenyl, benzyl oxalate, di(p-chlorobenzyl)oxalate, an equivalent mixture of benzyl oxalate and di(p-chlorobenzyl)oxalate, di(p-methylbenzyl)oxalate, an equivalent mixture of di(p-chlorobenzyl)oxalate and di(p-methylbenzyl)oxalate, 1-hydroxy-2-naphthoic acid phenyl ester, 1,2-diphenoxyethane, 1,2-di-(3-methylphenoxy) ethane, 1,2-bis(phenoxymethyl)benzene, dimethyl terephthalate, stearic acid amide, "amide AP-1" (a mixture of stearic acid amide and palmitic acid amide at 7:3), diphenylsulfone and 4-acetylbiphenyl.

More specifically, these sensitizers may be appropriately used at a ratio of 0.1 to 10 parts by mass relative to 1 part by mass of a dye. For example, a thermal recording paper can be produced by combining 2 parts by mass of a color-developing composition of the present invention and 1 part by mass of di(p-methylbenzyl)oxalate as a sensitizer, relative to 1 part by mass of 3-di(n-butyl)amino-6-methyl-7-anilinofluoran as a dye. Likewise, the sensitizers referred to above such as 1,2-di-(3-methylphenoxy)ethane, 1,2-bis(phenoxymethyl)benzene and diphenylsulfone may be combined.

As a filler, the followings can be used: silica, clay, kaolin, fired kaolin, talc, satin white, aluminum hydroxide, calcium carbonate, magnesium carbonate, zinc oxide, titanium oxide, barium sulfate, magnesium silicate, aluminum silicate, plastic pigment, etc. Particularly preferred for a recording material of the present invention is a salt of alkaline earth metal. A carbonate salt is further preferred, and calcium carbonate, magnesium carbonate, etc. are preferable. The ratio of filler for use is 0.1 to 15 parts by mass, preferably 1 to 10 parts by mass relative to 1 part by mass of the color-forming compound. In addition, the fillers referred to above can be mixed for use.

Examples of the dispersant include sulfosuccinic acid esters such as dioctyl sodium sulfosuccinate, dodecylbenzenesulfonic acid sodium, sodium salt of lauryl alcohol sulfate ester and a fatty acid salt.

Examples of the antioxidant include
2,2'-methylenebis(4-methyl-6-tert-butylphenol),
2,2'-methylenebis(4-ethyl-6-tert-butylphenol),
4,4'-propylmethylenebis(3-methyl-6-tert-butylphenol),
4,4'-butylidenebis(3-methyl-6-tert-butylphenol),
4,4'-thiobis(2-tert-butyl-5-methylphenol),
1,1,3-tris(2-methyl-4-hydroxy-5-tert-butylphenol)butane,
4-[4-{1,1-bis(4-hydroxyphenyl)ethyl}-α,α'-dimethylbenzyl]phenol,
1,1,3-tris(2-methyl-4-hydroxy-5-cyclohexylphenyl)butane,
2,2'-methylenebis(6-tert-butyl-4-methylphenol),
2,2'-methylenebis(6-tert-butyl-4-ethylphenol),
4,4'-thiobis(6-tert-butyl-3-methyl-phenol,
1,3,5-tris(4-(1,1-dimethylethyl)-3-hydroxy-2,6-dimethylphenyl)methyl-1,3,5-triazine-2,4,6(1H,3H,5H)-trione and
1,3,5-tris((3,5-bis(1,1-dimethylethyl)-4-hydroxyphenyl)methyl)-1,3,5-triazine-2,4,6(1H,3H,5H)-trione.

The desensitizer is exemplified by a fatty higher alcohol, polyethyleneglycol and guanidine derivative.

The antiadhesive agent is exemplified by stearic acid, zinc stearate, calcium stearate, carnauba wax, paraffin wax and ester wax.

Examples of the light stabilizer include: a salicylic acid-based ultraviolet absorber such as phenylsalicylate, p-tert-butylphenylsalicylate and p-octylphenylsalicylate; a benzophenone-based ultraviolet absorber such as
2,4-dihydroxybenzophenone, 2-hydroxy-4-methoxybenzophenone,
2-hydroxy-4-benzyloxybenzophenone,
2-hydroxy-4-dodecyloxybenzophenone,
2,2'-dihydroxy-4-methoxybenzophenone,
2,2'-dihydroxy-4,4'-dimethoxybenzophenone,
2-hydroxy-4-methoxy-5-sulfobenzophenone and
bis(2-methoxy-4-hydroxy-5-benzoylphenyl)methane; a benzotriazole-based ultraviolet absorber such as
2-(2'-hydroxy-5'-methylphenyl)benzotriazole,
2-(2'-hydroxy-5'-tert-butylphenyl)benzotriazole,
2-(2'-hydroxy-3',5'-di-tert-butylphenyl)benzotriazole,
2-(2'-hydroxy-3-tert-butyl-5'-methylphenyl)-5-chloro-benzotriazole,
2-(2'-hydroxy-3',5'-di-tert-amylphenyl)benzotriazole,
2-(2'-hydroxy-3',5'-di-tert-butylphenyl)-5-chlorobenzotriazole,
2-(2'-hydroxy-5'-tent-butylphenyl)benzotriazole,
2-(2'-hydroxy-5'-(1",1",3",3"-tetramethylbutyl)phenyl)benzotriazole,
2-[2'-hydroxy-3'-(3",4",5",6"-tetrahydrophthalimidomethyl)-5'-methylphenyl]benzotriazole,
2-(2'-hydroxy-5'-tert-octylphenyl)benzotriazole,
2-[2'-hydroxy-3',5'-bis(α,α'-dimethylbenzyl)phenyl]-2H-benzotriazole,
2-(2'-hydroxy-3'-dodecyl-5'-methylphenyl)benzotriazole,
2-(2'-hydroxy-3'-undecyl-5'-methylphenyl)benzotriazole,
2-(2'-hydroxy-3'-tridecyl-5'-methylphenyl)benzotriazole,
2-(2'-hydroxy-3'-tetradecyl-5'-methylphenyl)benzotriazole,
2-(2'-hydroxy-3'-pentadecyl-5'-methylphenyl)benzotriazole,
2-(2'-hydroxy-3'-hexadecyl-5'-methylphenyl)benzotriazole,
2-[2'-hydroxy-4'-(2"-ethylhexyl)oxyphenyl]benzotriazole,
2-[2'-hydroxy-4'-(2"-ethylheptyl)oxyphenyl]benzotriazole,
2-[2'-hydroxy-4'-(2"-ethyloctyl)oxyphenyl]benzotriazole,
2-[2'-hydroxy-4'-(2"-propyloctyl)oxyphenyl]benzotriazole,
2-[2'-hydroxy-4'-(2"-propylheptyl)oxyphenyl]benzotriazole,
2-[2'-hydroxy-4'-(2"-propylhexyl)oxyphenyl]benzotriazole,
2-[2'-hydroxy-4'-(1"-ethylhexyl)oxyphenyl]benzotriazole,
2-[2'-hydroxy-4'-(1"-ethylheptyl)oxyphenyl]benzotriazole,
2-[2'-hydroxy-4'-(1"-ethyloctyl)oxyphenyl]benzotriazole,
2-[2'-hydroxy-4'-(1"-propyloctyl)oxyphenyl]benzotriazole,
2-[2'-hydroxy-4'-(2"-propylheptyl)oxyphenyl]benzotriazole,
2-[2'-hydroxy-4'-(2"-propylhexyl)oxyphenyl]benzotriazole,
2,2'-methylenebis[4-(1,1,3,3-tetramethylbutyl)-6-(2H-benzotriazole-2-yl)phenol, and a condensate of polyethyleneglycol and
methyl-3-[3-tert-butyl-5-(2H-benzotriazole-2-yl)-4-hydroxyphenyl]propionate; a cyanoacrylate-based ultraviolet absorber such as 2'-ethylhexyl-2-cyano-3,3-diphenylacrylate and ethyl-2-cyano-3,3-diphenylacrylate; a hindered amine-based ultraviolet absorber such as bis(2,2,6,6-tetramethyl-4-piperidyl)sebacate, succinic acid-bis(2,2,6,6-tetramethyl-4-piperidyl)ester and
2-(3,5-di-tent-butyl)malonic acid-bis(1,2,2,6,6-pentamethyl-4-piperidyl)ester; and
1,8-dihydroxy-2-acetyl-3-methyl-6-methoxynaphthalene and its related compounds.

Examples of the fluorescent dye include
4,4'-bis[2-anilino-4-(hydroxyethyl)amino-1,3,5-triazinyl-6-amino]stilbene-2,2'-disulfonic acid disodium salt,
4,4'-bis[2-anilino-4-bis(hydroxyethyl)amino-1,3,5-triazinyl-6-amino]stilbene-2,2'-disulfonic acid disodium salt,
4,4'-bis[2-methoxy-4-(hydroxyethyl)amino-1,3,5-triazinyl-6-amino]stilbene-2,2'-disulfonic acid disodium salt,
4,4'-bis[2-anilino-4-(hydroxypropyl)amino-1,3,5-triazinyl-6-amino]stilbene-2,2'-disulfonic acid disodium salt,
4,4'-bis[2-m-sulfoanilino-4-bis(hydroxyethyl)amino-1,3,5-triazinyl-6-amino]stilbene-2,2'-disulfonic acid disodium salt,
4-[2-p-sulfoanilino-4-bis(hydroxyethyl)amino-1,3,5-triazinyl-6-amino]-4'-[2-m-sulfoanilino-4-bis(hydroxyethyl)amino-1,3,5-triazinyl-6-amino]stilbene-2,2'-disulfonic acid tetrasodium salt,
4,4'-bis[2-p-sulfoanilino-4-bis(hydroxyethyl)amino-1,3,5-triazinyl-6-amino]stilbene-2,2'-disulfonic acid tetrasodium salt,
4,4'-bis[2-(2,5-disulfoanilino)-4-phenoxyamino-1,3,5-triazinyl-6-amino]stilbene-2,2'-disulfonic acid hexasodium salt,
4,4'-bis[2-(2,5-disulfoanilino)-4-(p-methoxycarbonylphenoxy]amino-1,3,5-triazinyl-6-amino]stilbene-2,2'-disulfonic acid hexasodium salt,
4,4'-bis[2-(p-sulfophenoxy)-4-bis(hydroxyethyl)amino-1,3,5-triazinyl-6-amino]stilbene-2,2'-disulfonic acid hexasodium salt,
4,4'-bis[2-(2,5-disulfoanilino)-4-formalinylamino-1,3,5-triazinyl-6-amino]stilbene-2,2'-disulfonic acid hexasodium salt and
4,4'-bis[2-(2,5-disulfoanilino)-4-bis(hydroxyethyl)amino-1,3,5-triazinyl-6-amino]stilbene-2,2'-disulfonic acid hexasodium salt.

The present invention will be explained in more detail in the following with reference to the Examples, but the present invention shall not be limited to these exemplifications.

Reference Synthetic Example 1

To a 1 L four-neck recovery flask equipped with an agitator and a thermometer, water (14.5 g) and 8.0 g (0.20 mol) of NaOH were added and dissolved at 90° C. Thereto was added 25.0 g (0.10 mol) of 4,4'-dihydroxydiphenylsulfone (hereinafter abbreviated as 4,4'-BPS). The resultant solution was heated to 110° C. and added dropwise with 7.1 g (0.05 mol) of 2,2'-dichlorodiethyl ether (hereinafter abbreviated as DCEE) for 30 min. Upon completion of the dropwise addition, the solution was kept at 110° C. and subjected to a condensation reaction for 6.5 hours. Upon completion of the reaction, 250.0 g of water was added to the reaction solution which was then kept at room temperature and adjusted for pH by the addition of 20% $H_2SO_4$. After adjusting the pH, the reaction solution was refluxed for 1 hour at 90° C. and allowed to cool. Crystal was separated by filtration and dried under reduced pressure at 70° C. to obtain the composition having a compound represented by formula (I') as a main component with the yield of 22.8 g.

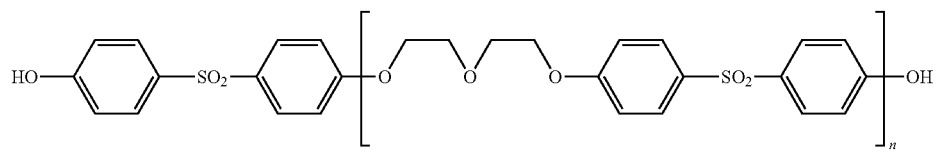

(wherein n represents any integer of 1 to 6)
(being a mixture of the n=1 compound to the n=6 compound, which contains the n=1 compound, 2,2'-bis[4-(4-hydroxyphenylsulfonyl)phenyloxy]diethylether, by 35% by mass)

Reference Synthetic Example 2

To a 3 L four-neck recovery flask equipped with an agitator and a thermometer, water (143.5 g) and 108.0 g (2.7 mol) of NaOH were added and dissolved at 90° C. Thereto was added 337.5 g (1.35 mol) of 4,4'-BPS. The resultant solution was heated to 110° C. and added dropwise with 16.2 g (0.11 mol) of DCEE for 30 min. Upon completion of the dropwise addition, the solution was kept at 110° C. and subjected to a condensation reaction for 4 hours. Upon completion of the reaction, 2000 g of water was added to the reaction solution which was then kept at room temperature. Then, the precipitate was removed by filtration. The solution was adjusted for pH by the addition of 20% $H_2SO_4$ and refluxed for 1 hour at 90° C. The precipitated solid was separated by filtration and dried under reduced pressure at 70° C. to obtain 2,2'-bis[4-(4-hydroxyphenylsulfonyl)phenyloxy]diethylether with the yield of 37.9 g.

Synthetic Examples of Molecular Compounds

Synthetic Example 1

To the reaction composition obtained in Reference Synthetic Example 1, 300 ml of 1,4-dioxane was added and heated to reflux for 3 hours. After allowing the resultant composition to cool to room temperature, 1,4-dioxane was distilled away under reduced pressure. The residue was further dried under reduced pressure at room temperature to obtain a composition containing a molecular compound consisting of 2,2'-bis[4-(4-hydroxyphenylsulfonyl)phenyloxy]diethylether and 1,4-dioxane in the compositional ratio of 1:1 (molar ratio). It was confirmed by TG/DTA, $^1$HNMR and X-ray diffraction pattern that the above molecular compound was contained. Further, it was confirmed by X-ray diffraction pattern that this compound contained a crystalline compound.

Synthetic Example 2

To the reaction composition obtained in Reference Synthetic Example 1, 300 ml of water was added and heated to reflux for 3 hours. After allowing the resultant composition to cool to room temperature, water was distilled away under reduced pressure. The residue was further dried under reduced pressure at room temperature to obtain a composition containing a molecular compound consisting of 2,2'-bis[4-(4-hydroxyphenylsulfonyl)phenyloxy]diethylether and water in the compositional ratio of 1:1 (molar ratio). It was confirmed by TG/DTA, $^1$HNMR and X-ray diffraction pattern that the above molecular compound was contained. Further, it was confirmed by X-ray diffraction pattern that this compound contained a crystalline compound.

Synthetic Example 3

To 2,2'-bis[4-(4-hydroxyphenylsulfonyl)phenyloxy]diethylether synthesized in Reference Synthetic Example 2, 300 ml of 1,4-dioxane was added and heated to reflux for 3 hours. After allowing the resultant composition to cool to room temperature, 1,4-dioxane was distilled away under reduced pressure. The residue was further dried under reduced pressure at room temperature to obtain a composition containing a molecular compound consisting of 2,2'-bis[4-(4-hydroxyphenylsulfonyl)phenyloxy]diethylether and 1,4-dioxane in the compositional ratio of 1:1 (molar ratio). It was confirmed by TG/DTA, $^1$HNMR and X-ray diffraction pattern that the above molecular compound was contained. Further, it was confirmed by X-ray diffraction pattern that this compound contained a crystalline compound.

Synthetic Example 4

To 2,2'-bis[4-(4-hydroxyphenylsulfonyl)phenyloxy]diethylether synthesized in Reference Synthetic Example 2, 300 ml of water was added and heated to reflux for 3 hours. After allowing the resultant composition to cool to room temperature, water was distilled away under reduced pressure. The residue was further dried under reduced pressure at room temperature to obtain a composition containing a molecular compound consisting of 2,2'-bis[4-(4-hydroxyphenylsulfonyl)phenyloxy]diethylether and water in the compositional ratio of 1:1 (molar ratio). It was confirmed by TG/DTA, $^1$HNMR and X-ray diffraction pattern that the above molecular compound was contained. Further, it was confirmed by X-ray diffraction pattern that this compound contained a crystalline compound.

(Powder X-Ray Diffraction)

Figure 2:
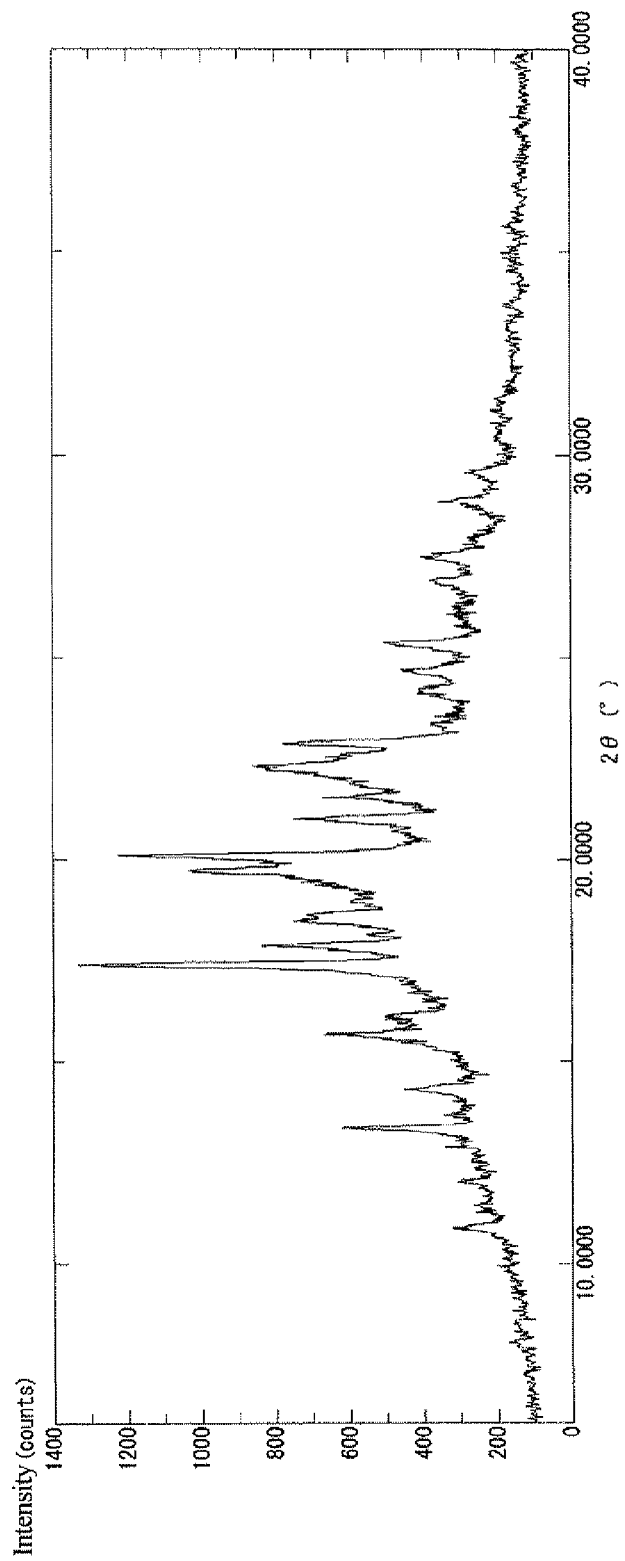
FIG. 2 shows the powder X-ray diffraction pattern of the composition obtained in Synthetic Example 2.
Figure 3:
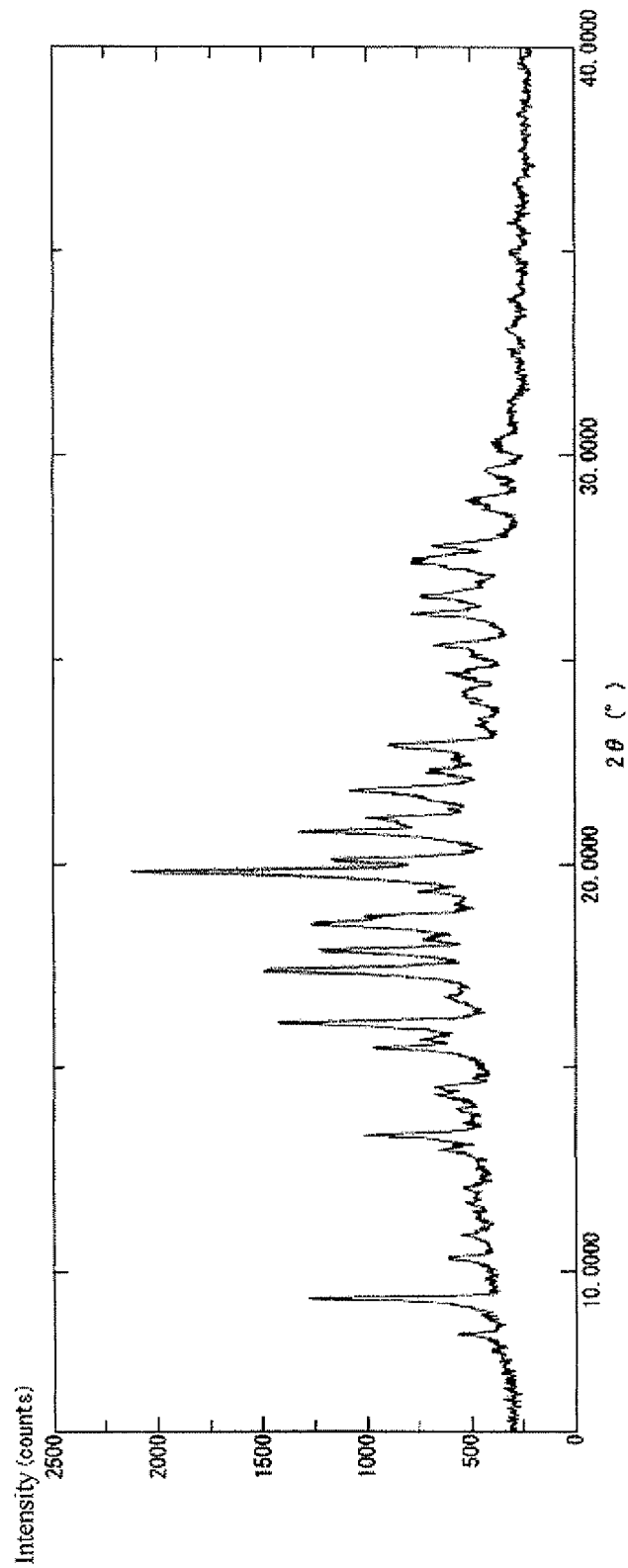
FIG. 3 shows the powder X-ray diffraction pattern of the composition obtained in Synthetic Example 3.
Figure 4:
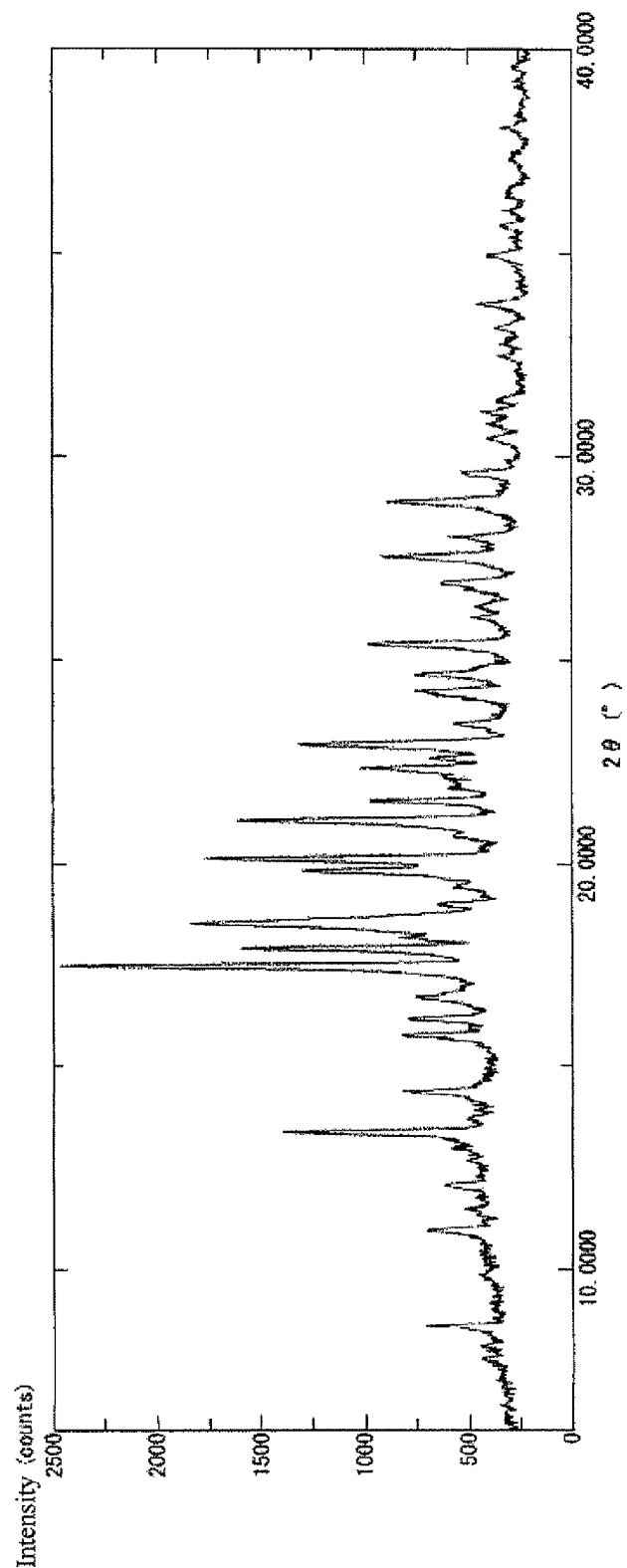
FIG. 4 shows the powder X-ray diffraction pattern of the composition obtained in Synthetic Example 4.

Each composition obtained in Synthetic Examples 1 to 4 was analyzed using Ultima IV (Rigaku Corporation), an X-ray diffraction device. The results are shown in FIGS. 1 to 4.

Production of Thermal Recording Paper

Example 1

Dispersion Solution of a Dye (Solution A)
3-Di-n-butylamino-6-methyl-7-anilinofluoran 16 parts
Aqueous solution of 10% polyvinylalcohol 84 parts Dispersion Solution of a Color-Developing Agent (Solution B)
Composition of Synthetic Example 1 16 parts
Aqueous solution of 10% polyvinylalcohol 84 parts
Dispersion Solution of a Filler (Solution C)
Calcium carbonate 27.8 parts
Aqueous solution of 10% polyvinylalcohol 26.2 parts
Water 71 parts First, mixtures of solutions A to C consisting of respective components were respectively ground well in a sand grinder to prepare the dispersion solutions of solutions A to C consisting of the respective components. A coating solution was prepared by mixing 1 part by mass of solution A, 2 parts by mass of solution B and 4 parts by mass of solution C. This coating solution was applied and dried on a white paper using a wire rod (Wire bar No. 12, Webster), followed by a calendar treatment to produce a thermal recording paper (coating solution: about 5.5 g/m² in terms of dry mass).

Example 2

A thermal recording paper was produced according to the method described in Example 1, except that the composition of Synthetic Example 2 was used instead of the composition of Synthetic Example 1 for Dispersion solution of a color-developing agent (solution B) in Example 1.

Example 3

A thermal recording paper was produced according to the method described in Example 1, except that the composition of Synthetic Example 3 was used instead of the composition of Synthetic Example 1 for Dispersion solution of a color-developing agent (solution B) in Example 1.

Example 4

A thermal recording paper was produced according to the method described in Example 1, except that the composition of Synthetic Example 4 was used instead of the composition of Synthetic Example 1 for Dispersion solution of a color-developing agent (solution B) in Example 1.

Comparative Example 1

A thermal recording paper was produced according to the method described in Example 1, except that the composition of Reference Synthetic Example 1 was used instead of the composition of Synthetic Example 1 for Dispersion solution of a color-developing agent (solution B) in Example 1.

Comparative Example 2

A thermal recording paper was produced according to the method described in Example 1, except that the composition of Reference Synthetic Example 2 was used instead of the composition of Synthetic Example 1 for Dispersion solution of a color-developing agent (solution B) in Example 1.

Test Example

<Thermal Assessment Test-Background Heat Resistance Test>

A part of the thermal recording paper respectively produced in Examples 1 to 4 and Comparative Examples 1 and 2 was cut off and kept in a thermostat device (YAMATO, Product name: DK-400) for 24 hours at 80° C. and 90° C., and then the background density (Macbeth value) of each test paper was measured. Table 1 collectively shows the results.

TABLE 1

|  | Background heat resistance test | |
|---|---|---|
|  | 80° C. | 90° C. |
| Example 1 | 0.13 | 0.28 |
| Example 2 | 0.11 | 0.17 |
| Comparative Example 1 | 0.17 | 0.41 |
| Example 3 | 0.08 | 0.11 |
| Example 4 | 0.07 | 0.08 |
| Comparative Example 2 | 0.16 | 0.19 |

INDUSTRIAL APPLICABILITY

By using a color-developing composition of the present invention as a recording material, a recording material can be provided that has a sufficient color-forming sensitivity, superior storage stability, and, in particular, an extremely little background fogging in a heat resistance test.

The invention claimed is:

1. A color-developing composition containing a molecular compound, wherein the molecular compound comprises as component compounds:
  $H_2O$; and
  a compound represented by formula (I):

$$HO-\underset{(R^1)_n}{\underset{|}{\bigcirc}}-S(O)_m-\underset{(R^2)_p}{\underset{|}{\bigcirc}}-O-Y-O-\underset{(R^3)_q}{\underset{|}{\bigcirc}}-S(O)_m-\underset{(R^4)_r}{\underset{|}{\bigcirc}}-OH \quad (I)$$

wherein:
  Y represents:
    a C1-C12 hydrocarbon group which is chained or branched and saturated or unsaturated, or
    a C1-C8 hydrocarbon group which is chained or branched, saturated or unsaturated and has an ether or thioether bond, or
  represents the following formula:

$$-R'-\bigcirc-R'- \quad \text{or} \quad -\underset{H_2}{C}-\underset{\underset{OH}{|}}{\overset{T}{C}}-\underset{H_2}{C}-$$

where:
  each R' may be the same or different and each represents a methylene group or ethylene group; and
  T represents a hydrogen atom or a C1-C4 hydrocarbon group:
  $R^1$, $R^2$, $R^3$, and $R^4$ each independently represents a C1-C6 alkyl group or C2-C6 alkenyl group;
  n, p, q, and r each represents any integer of 0 to 4; and
  m represents any integer of 0 to 2.

2. The color-developing composition according to claim 1, wherein the compound represented by formula (I) is a compound represented by formula (II):

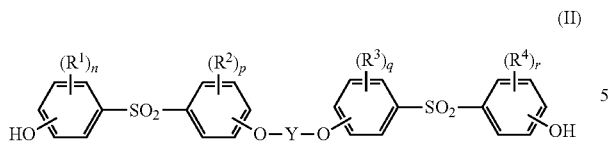

(II)

wherein Y, $R^1$-$R^4$, n, p, q and r have the same meaning as defined above.

3. The color-developing composition according to claim 1, wherein the compound represented by formula (I) is 2,2'-bis[4-(4-hydroxyphenylsulfonyl)phenyloxy]diethylether.

4. The color-developing composition according to claim 1, wherein the color-developing composition is a composition containing 2 or more types of products obtained by reacting 4,4'-dihydroxydiphenylsulfone and 2,2'-dichlorodiethylether.

5. The color-developing composition according to claim 1, which contains a molecular compound consisting of 2,2'-bis[4-(4 hydroxyphenylsulfonyl)phenyloxy]diethylether and $H_2O$, wherein the molecular compound is obtained by mixing the following (A) and (B):
  (A) a product obtained by reacting 4,4'-dihydroxydiphenylsulfone and 2,2'-dichlorodiethylether; and
  (B) $H_2O$.

6. A recording material containing the color-developing composition according to claim 1.

* * * * *